(12) United States Patent
Vieira (10) Patent No.: US 6,446,583 B2
(45) Date of Patent: Sep. 10, 2002

(54) EVAPORATION DEVICE FOR VOLATILE SUBSTANCES

(75) Inventor: Pedro Queiroz Vieira, Parede (PT)

(73) Assignee: C.T.R. Consultoria Técnica e Representacões Lda, Almargem do Bispo (PT)

( * ) Notice: Subject to any disclaimer, the term of this patent is extended or adjusted under 35 U.S.C. 154(b) by 0 days.

(21) Appl. No.: 09/739,981

(22) Filed: Dec. 18, 2000

(30) Foreign Application Priority Data

Dec. 18, 1999 (EP) .......................................... 99125293

(51) Int. Cl.[7] .......................................... A01M 13/00
(52) U.S. Cl. ............................. 122/366; 261/DIG. 17; 392/392; 392/395; 43/129
(58) Field of Search ................ 122/366; 126/358.1, 126/350.2, 263.01, 96; 261/DIG. 17, DIG. 65; 392/386, 392, 394, 395, 403, 412; 43/129

(56) References Cited

U.S. PATENT DOCUMENTS

| | | | |
|---|---|---|---|
| 4,891,904 A | * 1/1990 | Tabita | 43/112 |
| 5,290,546 A | * 3/1994 | Hasegawa et al. | 392/395 |
| 6,141,496 A | * 10/2000 | Sundberg et al. | 392/392 |
| 6,236,807 B1 | * 5/2001 | Ruffolo et al. | 392/392 |
| 6,278,840 B1 | * 8/2001 | Basaganas Millan | 392/395 |

FOREIGN PATENT DOCUMENTS

| | | | |
|---|---|---|---|
| EP | 0 943 344 A1 | 9/1999 | A61L/1/20 |
| EP | 0 962 132 A1 | 12/1999 | A01M/9/03 |
| WO | WO 98/19526 | 5/1998 | A01M/9/03 |
| WO | WO 98 58682 A | 12/1998 | A61M/9/03 |

* cited by examiner

*Primary Examiner*—Gregory Wilson
(74) *Attorney, Agent, or Firm*—McNair Law Firm, P.A.; Cort Flint (57) ABSTRACT

An evaporation device 2 is disclosed for the evaporation of volatile substances, in particular insecticides and aromatics, which includes a housing 13 which contains a heating element and a container 50 for a substance to be evaporated. This container 50 contains a wick which is associated with the heating element with a wick end 30 protruding from container 50. The heating element can be longitudinally displaced near the container 50 in the housing 13 relative to the wick end 30 to adjust the degree of evaporation. According to the invention, the heating element is carried on a movable heater assembly that can be displaced longitudinally in the housing relative to the wick end. The movable heater assembly can be fixed in different positions relative to the wick end 30 and the longitudinal direction of the wick axis for the adjustment of the degree of evaporation.

20 Claims, 5 Drawing Sheets

EVAPORATION DEVICE FOR VOLATILE SUBSTANCES

BACKGROUND OF THE INVENTION

The present invention relates to a device for evaporating volatile substances, in particular insecticides and/or aromatics.

Insecticide and aromatic evaporation devices are generally known. For example, evaporation devices are known where a small plate introduced into an evaporation device and impregnated with an active ingredient is heated in order to evaporate the active ingredient. Furthermore a method is also known by which a container containing a volatile substance is introduced into a housing of an evaporation device. This container comprises a wick that conveys the substance to be evaporated by means of capillary action out of the container, whereby the wick end protruding from the container is located next to a heating element such as a ceramic block The substance is evaporated through the heat radiated by the ceramic block and can escape from the housing into the environment through aeration slits in the housing.

A disadvantage with the prior evaporation devices is that it is not possible to adapt the degree of evaporation to the prevailing room conditions or to the different sensitivities of persons present in the room. Thus, for example, in smaller rooms with insufficient air ventilation, it is desirable to lower the degree of evaporation, and this is not possible with prior evaporation devices. Furthermore adjustability of evaporation is especially desirable for insecticides, so that the degree of evaporation can be adjusted in accordance with the sensitivity of persons present in the room. This has also not been possible with the prior devices.

In order to be able to adjust the degree of evaporation to the appliwire requirements it is known to control the degree of evaporation by adjusting the heating output. Evaporation devices of that type are relatively expensive to manufacture, and are prone to malfunctions.

It is known in prior evaporation devices that the relative distance between the heating element and wick can be changed to adjust the degree of evaporation while the heating output is maintained constant (EP 0 943 344 A1). The evaporation device includes a resistance heating element with a connecting plug that is threaded into a housing element in which a container of the substances to be evaporated is located. Pin openings are provided on the housing element into which locking pins are inserted in such manner that they mesh with the threads of the plug. The distance between the resistance-heating element and a wick end protruding from the container can be changed by twisting the plug element. The plug element can be mounted eccentrically in the housing element, so that it too can be used to change the relative distance between the wick end and the resistance heating element to achieve the desired degree of evaporation. However, this method of adjusting the degree of evaporation is relatively complicated in construction and expensive to manufacture.

Another type of evaporation device in which the heating output remains constant and the relative distance between the wick and the heating element can be adjusted is known from WO 98/19526. The evaporation device comprises a housing into which a container with a wick can be screwed. The container is connected via a bushing to a swivel arm that moves in a guide slot, extending radially at an angle to the horizontal in the housing wall. Through the coupling of the swivel arm to the container the container is lifted relative to the housing in the axial direction when the swivel arm is turned radially. The wick end protruding form the container may be shifted relative to the fixed heating element. On the whole, this is a relatively expensive and complicated construction with a great number of additional components, so that the evaporating device is also expensive to manufacture.

It is therefore an object of the invention to provide an evaporation device for volatile substances, in particular insecticides and/or aromatics, which is simple in structure and can be produced economically yet the degree of evaporation can be easily adjusted to meet current requirements.

The above object is accomplished according to the present invention by providing a heating element carried on a movable heater assembly mounted in the housing. The heating element may be displaced longitudinally relative to the wick axis and can be fixed in different longitudinal positions relative to the wick end for the adjustment of the degree of evaporation. The heating element is advantageously designed as having simultaneously a double function by serving as a heating element and as a movable heater assembly so that the degree of evaporation can easily be adjusted by displacing the assembly in the longitudinal direction along the wick axis. In addition, this integration of functions makes it possible to achieve an overall space-saving and compact structure without significant expenditure for components and material. The already present components are used to adjust the degree of evaporation. An evaporation device of this type is especially well suited for small installation situations. The degree of evaporation can be adapted individually and easily to the appliwire requirements, and in addition the operation is simple and functioning is reliable.

In principle, several possibilities exist for mounting the heating element on the movable heater assembly capable of longitudinal displacement in the direction of the wick axis. In a preferred embodiment the heating element can be fixed on the housing by means of a clamp connection and/or a locking connection snapped. In another preferred embodiment, the movable heater assembly is fixed in a longitudinal position of the wick by means of a snap-in locking connection. The snap-in locking connection provides a secure holding within a given adjustment range. The greatest possible reliability of function is achieved in the sense that on the one hand the degree of evaporation can be adjusted continuously if necessary by simply pressing down the locking connection while on the other hand assurance is provided that the movable heater assembly is held securely in the desired position.

In a preferred embodiment the movable heater assembly is provided with at least one guide arm extending generally perpendicular to the wick axis. The arm is installed with one end of the guide arm in a slot opening in the housing wall for access from the outside of the housing. The guide arm can be made economically without significant expenditure on the movable heater assembly. In addition, the guide arm can serve as an indicator of the currently set distance between the heating element and the wick end by its position in the slot opening, possibly in combination with a scale on the housing area surrounding the slot opening. The guide arm is easily accessible on the other side through such a slot opening for easy maintenance.

At least one guide arm may be used advantageously, held in the slot opening between two end stop positions in the housing wall. To provide an advantageous targeted and controlled guiding of the movable heater assembly, the guiding device may be provided with two guide arms connectable to opposing housing sides. The reliability of function of the movable heater assembly is further enhanced.

The linear guide device preferably has a first guide element on each guide arm approximately parallel to the longitudinal direction of the wick axis. There is a second guide element on the housing corresponding to each first guide element. The first guide element may be in the form of a guide groove and the second guide element in the form of a guide ridge which slides in the guide groove, or vice-versa. To ensure especially simple and reliable positioning, and at the same time simple displacement, the guide ridge may be guided with a friction lock in the guide groove. Advantageously, snap-in openings may be made on the guide ridge, spaced to correspond to different longitudinal distance settings. A snap-in protrusion of the movable heater assembly may be snapped into the opening at a given distance from the wick end to further enhance reliability.

Advantageously, at least one guide arm of the movable heater assembly, approximately perpendicular to the longitudinal direction of the wick axis, carries an electrical heating element. A heating element of this type may be formed by an electric resistance or, in a preferred embodiment, in the form of a ceramic block. Good performance of the entire evaporation device results with the electric heating element in the form of a ceramic block coupled with electric wires. The ceramic block may be mounted on a supporting plate connected to at least one guide arm and can be held in place by means of an elastically attached locking arm. The elastic locking arm may be pre-stressed in the direction of the ceramic block and surrounding the ceramic block laterally in shape of an "L." Complimentary seating ridges formed on the block and supporting plate, preferably made of plastic, make it possible that heat bridges with small surfaces engaging the supporting plate are created. The heat radiation of the ceramic block in the direction of the wick is thus optimized. The locking arms provide secure holding of the ceramic block on the supporting plate in that they can be simply snapped into the latter. Preferably four locking arms are installed on the supporting plate for especially secure holding. In a preferred embodiment, with two guide arms across from each other, the supporting plate is approximately in the center between the two guide arms and in the center of the housing.

A passage for the wick may be made in the ceramic block and correspondingly in the supporting plate. The wick end can be moved through the passage according to the distance that has been selected. The wick passage may, for example, be a circular hole, or a perpendicular recess on the edge. In another advantageous embodiment a distance and/or operational indicator visible through a corresponding opening in the housing be provided on the movable heater assembly. An electric light, e.g. a glow lamp, is preferably provided as the distance and/or operational indicator. In this manner it is can easily be seen from the outside whether the evaporation device is in operation, which is especially advantageous in case an ON/OFF switch is present. At the same time, it can also be used to easily read the position of the movable heater assembly by means of a scale disposed in the area of the housing opening.

Basically, the movable heater assembly can be adjusted continuously or at different incremental positions at different distances from the wick end. In an advantageous embodiment, the movable heater assembly can be displaced between two limit positions constituted by stops formed on the housing side. The movable heater assembly may be located in immediate proximity to the wick end in a first end stop position for a maximum degree of evaporation. The movable heater assembly is preferably located at a distance from the upper wick end as seen from above the wick end in the longitudinal direction of the wick to achieve minimum evaporation. The movable heater assembly may preferably be held in intermediate positions between the two limit positions so that a good individual adjustment of the degree of evaporation to the appliwire requirements is achieved.

The housing itself can be made in different manners depending on the different embodiments. In one advantageous embodiment, the housing has aeration slits and is constructed in a forward housing shell and a rear housing shell removably connected to each other via corresponding locking elements in a locking connection. The rear housing shell may be formed by two housing half-shells which are detachably connected to each other also via corresponding locking elements in a locking connection. In a preferred embodiment, a plane of separation between the half-shells of the rear housing shell is located approximately in a central longitudinal area of the rear housing shell. Preferably the movable heater assembly is mounted on the housing so that it can be displaced longitudinally in the direction of the longitudinal wick axis after assembly or connection of the housing half-shells. The division of the rear housing shells into two housing half-shells makes an easy assembly of the movable heater assembly possible. Thus, for instance, it is possible to thread the guide grooves first on one guide ridge of a first housing half-shell, where two guide arms face each other, and then to install the second housing half-shell on this pre-assembled component. The guide ridge of this second housing half-shell then correspondingly engages the free guide groove of the free guide arm. This results in much greater ease of assembly. The ventilation slits are advantageously made in a housing area near the wick end, so that the evaporated substances can escape upwardly from the housing into the environment.

In principle, connecting the movable heater assembly with electric wires presents no problem in the design according to the invention. The displacement of the movable heater assembly is not so long that an excessive expenditure would be required for long wire lengths to accommodate displacements of the device. However, in order to shield the wires, among other things, from the housing interior in which the container is located, the rear housing shell is made with a double wall when mounted so as to create a wire channel in an advantageous embodiment. The wires can be stowed away in such a wire channel as they go from the heating element to a connection plug so they are shielded from the housing interior. This also ensures that the electrical wires are not in the way when the container is inserted into the housing interior. The rear wall constituting the outer housing wall may be provided with an opening to seat a connection plug so that it an be plugged into a socket. The connection plug in this opening is preferably inserted by means of a complimentary groove and ridge, preferably when the housing half-shells are assembled. In this case, the electric wires go from the connection plug through the wire channel to the heating element. In an especially advantageous embodiment the wires can be fixed in the wire channel in such manner that the wires are somewhat stretched in the second end stop position at maximum distance between the movable heater assembly and the wick end. In this way the longitudinal displacement of the heating element presents no problem with regard to wire lengths due to its longitudinal displacement. Alternately, a passage for the wires may be provided in the rear wall, instead of an opening for a connection plug, so that the housing can also be connected by a wire plugged into a socket far removed from the point of installation.

For simple insertion of the container in the housing with good access, a receiving slot or opening may be provided in the lower housing area through which the container can be introduced and/or screwed into the housing interior where it can be fixed or preferably snapped in detachably. Alternately, it is also possible to provide a passage for the wires in the rear wall instead of an opening for a connection plug so that the housing can be connected by a wire plugged into a socket removed from the point of installation.

For simple insertion of the container in the housing with good access, a receiving slot or opening may be provided in the lower housing area through which the container can be introduced and/or screwed into the housing interior where it can be fixed or preferably snapped in detachably.

DESCRIPTION OF THE DRAWINGS

The construction designed to carry out the invention will hereinafter be described, together with other features thereof.

The invention will be more readily understood from a reading of the following specification and by reference to the accompanying drawings forming a part thereof, wherein an example of the invention is shown and wherein.

DESCRIPTION OF A PREFERRED EMBODIMENT

Referring now in more detail to the drawings, the invention will now be described in more detail.

Figures 1, 2:
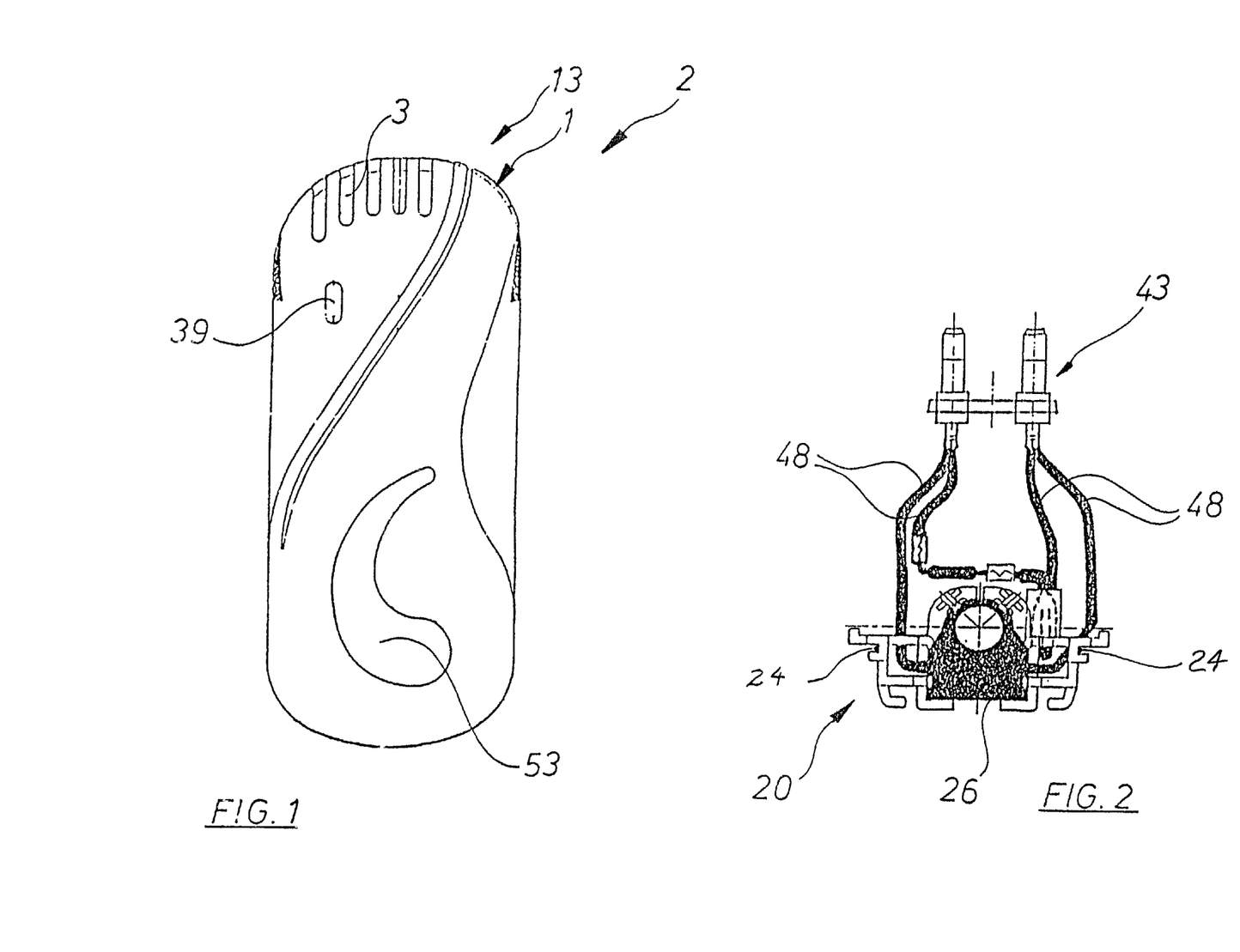
FIG. 1 is a schematic top view on a forward housing shell.
FIG. 2 is a schematic top view on a connection plug which is coupled via electric wires to a heating element made in form of a movable heater assembly, FIG. 3 schematically shows two housing half-shells which constitute a rear housing shell, FIG. 4 schematically shows the two housing half-shells according to FIG. 3 in an assembled state, FIG. 5 schematically shows a rear housing shell with a heating element made in form of a movable heater assembly that can be displaced longitudinally along it, in a first end stop position, FIG. 6 schematically shows a rear housing half with a heating element made in form of a movable heater assembly that can be displaced longitudinally along it, in a second stop position.

FIG. 1 is a schematic top view of a forward housing shell 1 of an evaporation device 2. This forward housing shell 1 has several aeration slits 3 at an upper end, through which an evaporated substance can escape into the environment. In addition, the forward housing shell 1 has also an opening, in this case drop shaped for example, to serve as a fullness indicator 53, e.g. in combination with a transparent cover or container.

FIG. 2 schematically shows a top view of an electric connection plug 43 that is coupled via electric wires 48 to a heating element 26 carried on a movable heater assembly 20, to be explained further below.

Figure 3:
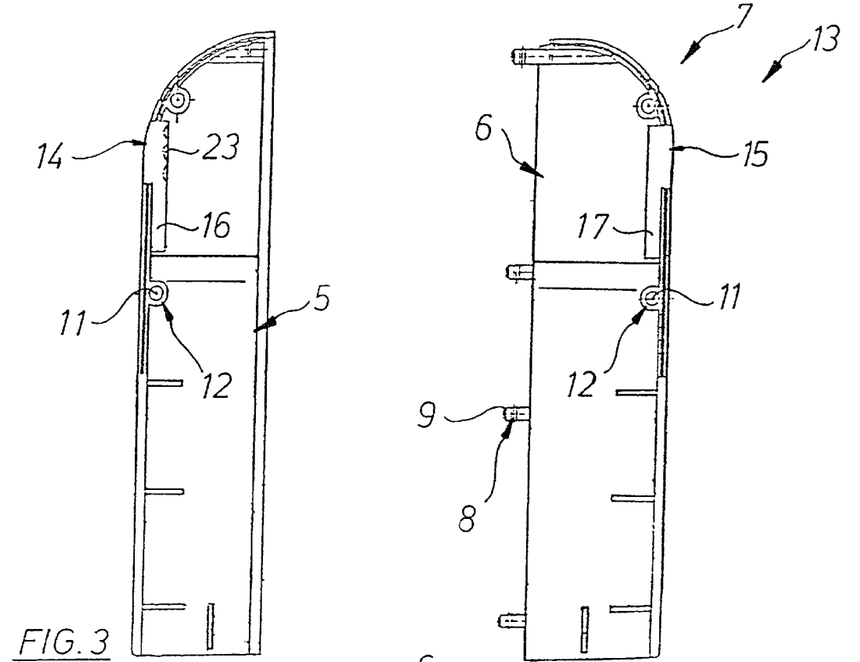
Figure 4:
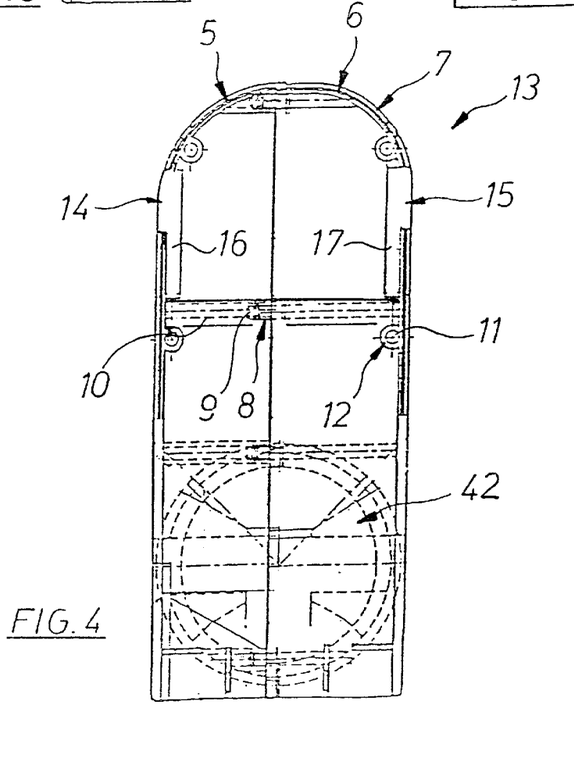

FIGS. 3 and 4 show a rear housing shell 7 consisting of two housing half-shells 5, 6 which can be connected detachably to each other by means of several locking connections 8. Each locking connection 8 consists of a locking pin 9 on the housing half-shell 6 that enters a corresponding locking seat 10 on the housing shell 5. Instead of the design of the locking pins 9 on the housing half-shell 6, the locking pins 9 can also be formed on the housing half-shell 5. Similarly it is also possible for the locking pins 9 and the seats 10 to alternate on the housing half-shell 5 as well as on the housing half-shell 6. The locking pins 9 are advantageously slightly bigger than the seats 10 to form a tight locking connection.

As can further be seen in FIGS. 3 and 4, additional locking pin seats 11 are formed on housing half-shells 5, 6 of rear housing shell 7 which receive locking pins (not shown) of a locking connection 12. Connection 12 is correspondingly formed on forward housing shell 1 and can be connected in the manner described above for the locking connections 8. When connected, rear housing shell 7 and forward housing shell 1 form a multi-part housing 13.

As can further be seen in FIGS. 3 and 4, slot openings 14, 15 are provided in upper portions of housing half-shells 5, 6 of rear housing shell 7 at the same level. Each slot opening 14, 15 includes a longitudinal guide ridge 16, 17 extending inwardly of the housing which extend longitudinally an upper slot opening edge to an area below the lower slot opening edge. As can best be seen in FIGS. 5 and 6 in combination with FIGS. 7 and 8, guide arms 18, 19 of a heating element, made in the form of movable heater assembly 20, include linear guide grooves 21, 22 corresponding to linear guide ridges 16, 17. Linear guide grooves 21, 22 slidably receive guide ridges 16, 17 for relative longitudinal movement. As can best be seen in FIG. 3, several locking index seats 23 can be formed on one or both guide ridges 16, 17. Index seats 23 receive a locking projection 24 formed by an edge of guiding device 20 within guide grooves 21, 22. Projection 24 can be snapped into an index seat 23 to hold the movable heater assembly 20 at a desired vertical position.

Figure 6:
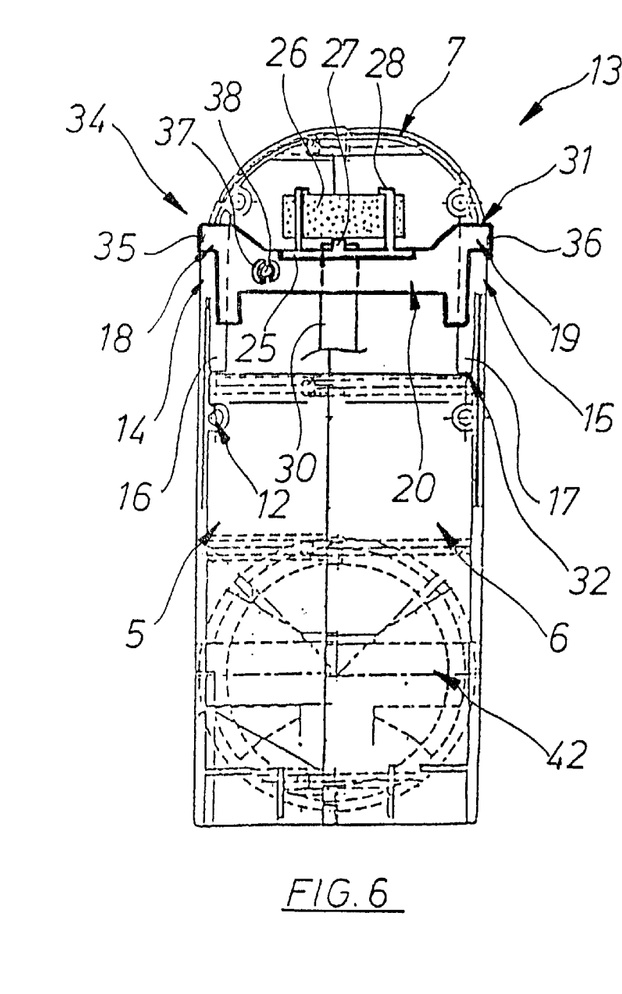
Figure 7:
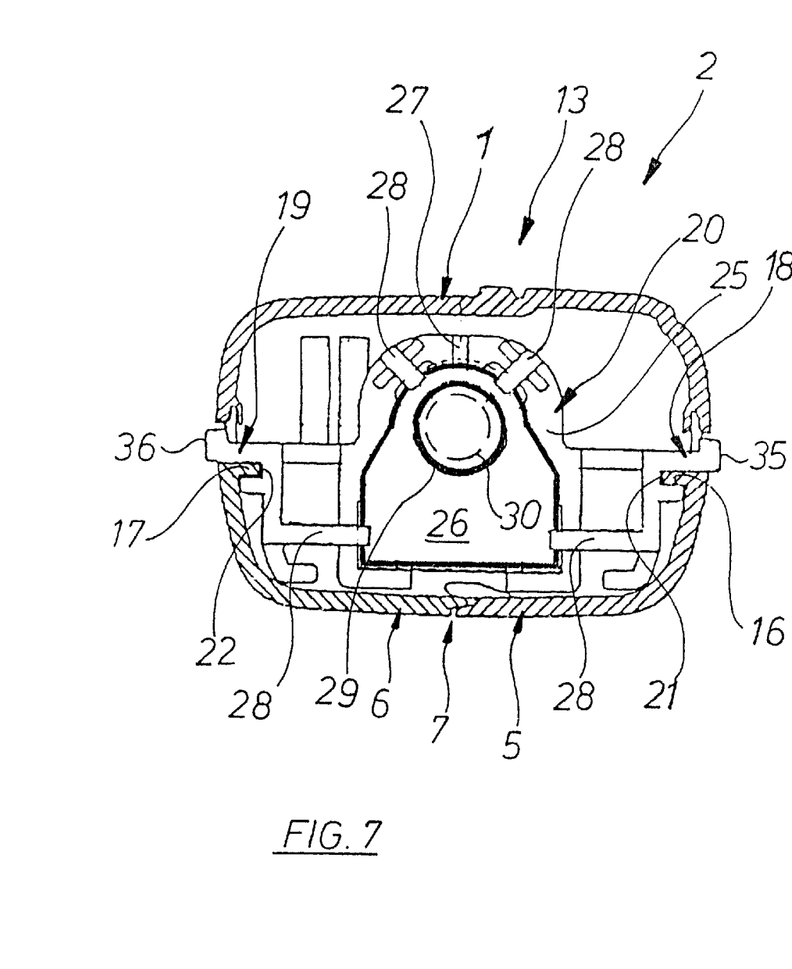
FIG. 7 shows a schematic cross-section through a completely assembled evaporation device with a top view on the heating element made in form of a movable heater assembly with a ceramic block.
Figure 8:
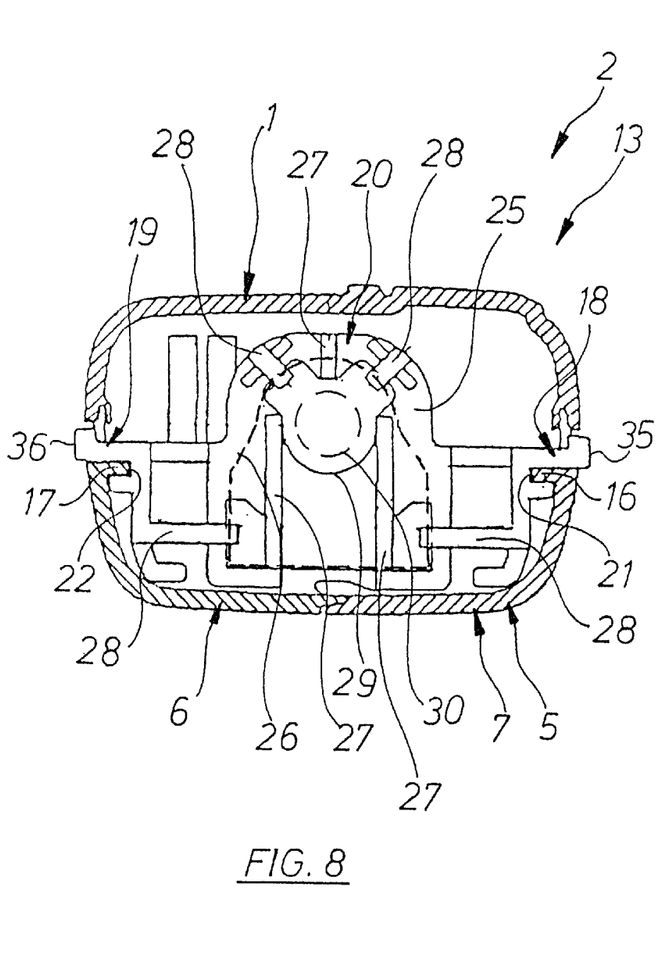
FIG. 8 is the representation of FIG. 8 without ceramic block.

Movable heater assembly 20 includes a supporting carrierplate 25 in a central area between guide arms 18, 19, as can best be seen in FIGS. 7 and 8, which show a cross-section of a completely assembled evaporation device 2. A ceramic block 26, serving as the heating element, is carried on this supporting plate 25. FIG. 8 shows a representation of the ceramic block 26 of FIG. 7 as indicated by broken lines. As can best be seen in FIGS. 5 to 8, ceramic block 26 is supported via rib 27 on plate 25 and by four locking arms 28 distributed over the circumference of the supporting plate 25. Locking arms 28 are made of a plastic material, just as housing 13 and the guide arms 18, 19. Locking arms 28 are connected elastically and pre-stressed on the supporting plate 25 toward ceramic block 26. In a snapped-in state, locking arms 28 surround the ceramic block 26 approximately in the form of an L, as can best be seen in FIGS. 5 and 6. In FIGS. 7 and 8 it can further be seen that ceramic block 26 and supporting plate 25 are each provided with a passage 29, aligned with each other, and extending through the block and plate. As is shown in part and schematically in FIGS. 5 and 6, a wick end 30 extending from the container is inserted through passage 29 formed in supporting plate 25 and ceramic block 26. The container contains a substance to be evaporated and a wick is inserted in housing 13 communicating with the wick.

Movable heater assembly 20 can be displaced between a first end stop position 33 (FIG. 5) and a second end stop position 34 (FIG. 6), as seen in the longitudinal direction of the wick. First and second end stop positions 33, 34 are provided by stops 31, 32 formed on the housing sides. The stops may be formed by the interaction of the slot opening areas facing each other in the longitudinal direction, in combination with corresponding guide arm ends 35, 36 of guide arms 18, 19. Guide arm ends 35, 36 extend through slot openings 14, 15 in such manner that they can easily be grasped with fingers from the outside of the housing. In first end stop position 33 (FIG. 5), ceramic block 26 immediately surrounds wick end 30 so that a maximum degree of evaporation is provided. On the other hand, in second end stop position (FIG. 6), ceramic block 26 is located above wick end 30, and only a low degree of evaporation is attained since heat emitted by ceramic block 26 acts only in part on wick end 30. Of course, it is also possible to provide intermediate positions of the movable heater assembly 20 between these two extreme positions shown in FIGS. 5 and 6, whereby the locking index seats 23 predetermine these intermediate positions.

Figure 5:
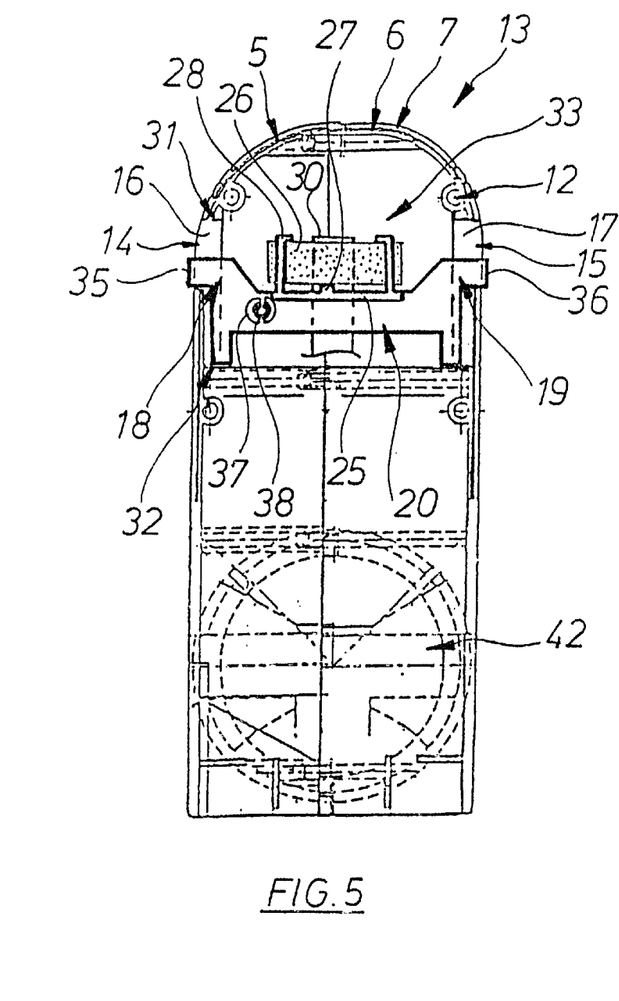

As can best be seen in FIGS. 5 and 6, an electric lamp 38 is carried on the guide arm 18, in a screening housing 37, which serves as a distance and/or operational indicator and is associated with a housing opening 39 (FIG. 1). In this manner, lamp 38 serves, for example in combination with an ON/OFF switch, on the housing as an indicator of the operational state or as a position indicator showing the degree of evaporation Depending on the position of lamp 38 relative to the housing as seen through the housing opening 39, and possibly in combination with a scale provided in an edge area of the housing opening 39, an indication of the degree of evaporation may be provided. Alternatively or in addition, such a scale can also be provided on the outside of the housing in the vicinity of slot openings 14, 15.

By constructing rear housing shell 7 from half-shells 5, 6, movable heater assembly 20 can be assembled easily. It is possible, for example, to interconnect movable heater assembly 20 together with linear guide groove 21 on linear guide ridge 16 of housing half-shell 5 and to then plug the second housing half-shell 6 on housing half-shell 5, whereby linear guide ridge 17 of the housing half-shell 6 enters the linear guide groove 22 of the guide arm 19. As a result, heating element 20 made in the form of a movable heater assembly is mounted on housing 13 so as to be capable of displacement in the longitudinal direction of the longitudinal wick axis once the two housing half-shells 5, 6 have been joined together.

As can be seen in particular in FIG. 9, which shows a schematic longitudinal cross section through a completely assembled evaporation device 2, the rear housing shell 7 is made with a double wall in its assembled state in an area below the movable heater assembly, with a wire channel 40 being thus formed.

A rear wall 42 of the rear housing shell 7 which constitutes the outer wall in this double-wall housing area comprises in this case an opening 42 which is shown in broken lines also in FIGS. 4 to 6. A connection plug 43 can be inserted into this opening 42 when the two housing half-shells 5, 6 are joined together via a groove-ridge pair 44. This groove-ridge pair 44 comprises on the rear wall 41 a ring-shaped ridge 45 going all around when the two housing half-shells 5, 6 are joined together and engaging a corresponding ring-shaped recess 46 on the connection plug 43 when assembled. Holding arms 47 which protrude into the recess 42 and are formed on in the area of the rear wall 41 to make additional locking of the connection plug in the rear wall 41 possible can be provided advantageously.

Electrical wires which are not shown here go in the wire channel 40 from the connection plug 43 to the ceramic block 26 of the heating element 20 made in form of a movable heater assembly. An electric wire can also go here from the electric connection plug 43 to the electric lamp 38.

In this case the electric wires in the wire channel 40 can be held in such manner between the locking pin seats 10 of the locking connection 12 and the inner wall of the rear wall 41 that the wires are slightly stretched for the maximum distance between the movable heater assembly 20 and the wick end 30 in the second end stop position 34.

A schematic representation of the connection plug 43 with the heating element 20 made in form of a movable heater assembly and in particular electric wires 48 going to the ceramic block 26 and to the electric lamp 38 are shown in FIG. 2 their disassembled state in a top view.

Figure 9:
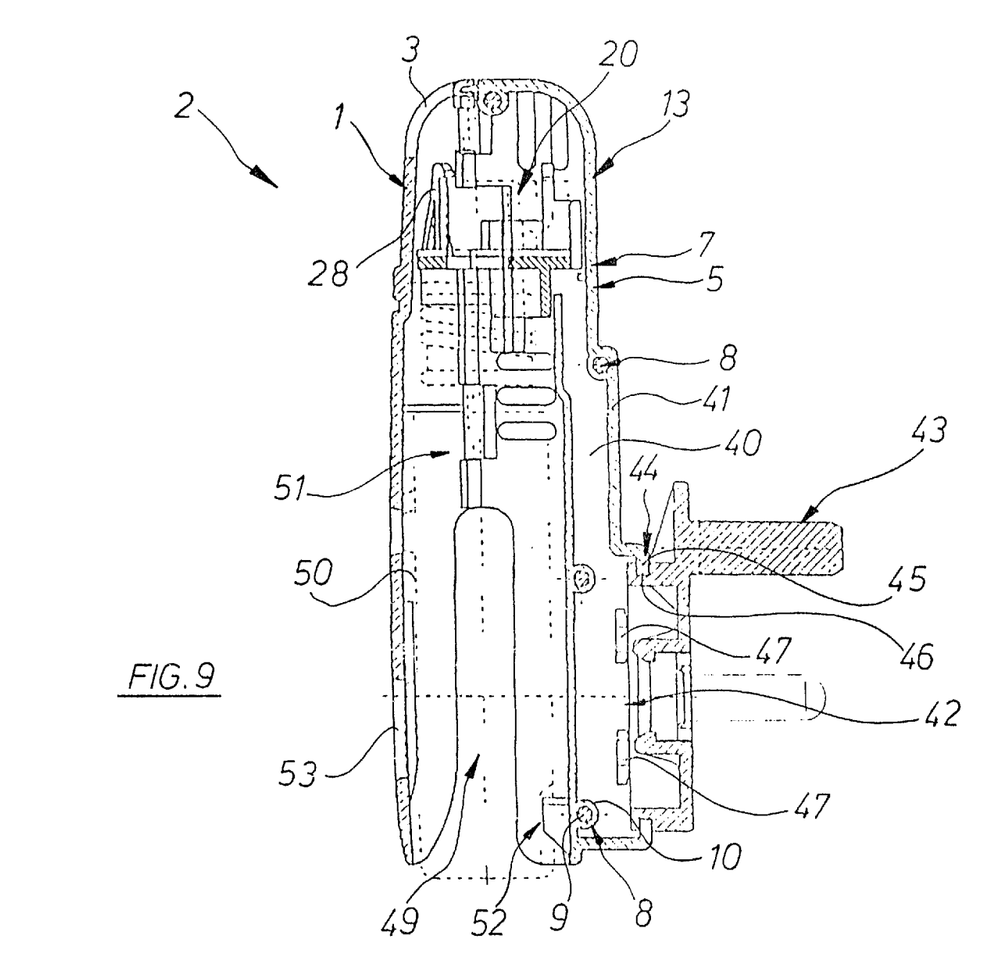
FIG. 9 shows a schematic longitudinal section through a completely assembled evaporation device with the container for a substance to be evaporated shown schematically by broken lines.

FIG. 9 furthermore shows schematically and in broken lines that the housing 13 is provided with a receiving slot 49 in a lower housing area through which a container 50 shown here only schematically and by broken lines can be introduced at least partially into the interior housing space 51 and can be fixed there detachably. The detachable attachment is effected e.g. through a locking connection 53 located in the lower receiving slot area.

What is claimed is:

1. An evaporation device for evaporating volatile substances such as insecticides and aromatics of a type having a housing containing a heating element, with a container for the volatile substance to be evaporated disposed in the housing, a wick which can be heated by the heating element with a wick end protruding from the container along a wick axis, whereby the heating element can be displaced relative to the wick end for an adjustment of the degree of evaporation, and wherein the improvement comprises:

a moveable heater assembly carried within the housing for longitudinal displacement relative to the wick axis and relative to the housing;

a heating element carried by said moveable heater assembly in a manner that said heating element is adjacent a portion of said wick end for heating said wick portion; and an adjustable connection operatively associated with said heater assembly for positioning said heater element at different axial positions relative to the wick end and the wick axis to adjust the degree of evaporation.

2. The device of claim 1, including a locking connection for affixing said heating element on the moveable heater assembly.

3. The device of claim 2 wherein said movable heater assembly includes at least one guide arm extending transverse having one guide arm end received in a slot opening formed in the housing wall for access from the outside of the housing.

4. The device of claim 3, including a first guide element carried by the heater assembly extending generally parallel to the direction of the wick axis, a second guide element carried by the housing, and said first and second guide elements intergaging with each other to guide movement of said heater assembly.

5. The device of claim 4 wherein said first guide element includes a linear guide groove, and said second guide element includes a guide ridge received within said guide groove; and a plurality of spaced locking openings formed on said guide ridge, a locking projection carried in said guide groove for engaging one of said locking openings to hold said movable heater assembly at a given distance relative to the wick end.

6. The device of claim 1 wherein said movable heater assembly includes at least one guide arm extending transverse to the longitudinal direction of the wick axis, and said heating element being carried on said one guide arm.

7. The device of claim 6, wherein said heating element includes a support plate, said ceramic block being carried by said support plate; at least one elastic locking arm carried by said support plate biased in the direction of the ceramic block which engaged said ceramic block; and a wick passage formed in said ceramic block through which the wick end can be moved.

8. The device of claim 1, including an indicator carried by said housing for indicating the relative position of said movable heater assembly and said wick end.

9. The device of claim 1, including a pair of spaced end stops between which said movable heater assembly is longitudinally displaced in such manner that said first end stop positions said movable heater assembly in close proximity to the wick end for a maximum degree of evaporation, and said second end stop positions said movable heater assembly at a distance above an upper wick end in the longitudinal direction of the wick axis for a minimum degree of evaporation.

10. The device of claim 1, including aeration slots formed in said housing.

11. The device of claim 10, wherein the housing includes a receiving slot formed in a lower housing area through which a container can be introduced and affixed within the housing interior.

12. The device of claim 1 wherein and said housing includes a forward housing shell and a rear housing shell, locking elements for joining said forward and rear shells to each other in such manner as to be detectable, and said rear housing shell includes two housing half-shells detachably joined together by means of a locking connection in such manner that mounting of said moveable heater assembly in the housing is facilitated.

13. The device of claim 12, wherein said rear housing shell includes a double wall in an area below said moveable heater assembly which has a wire channel therein.

14. The device of claim 13, said double wall includes a rear wall of the housing, a plug opening formed in said outer wall for receiving an electrical connection plus which connects to a wall plug.

15. The device of claim 14, including electrical wires routed through said wire channel from the connection plus to the heating element so that the wires are held in the wire channel with a sufficient length to accommodate displacement of said moveable heater assembly to said first end stop position.

16. An evaporation device for evaporating volatile substances such as insecticides and aromatics comprising:
   a housing;
   a container for the volatile substance to be evaporated disposed in the housing, and a wick having a wick end protruding from the container along a wick axis,
   a heating element for heating at least a portion of the wick end;
   a movable heater assembly carried within the housing for movement in the direction of the wick axis relative to the wick end and the housing; and
   said heating element being carried for movement with said movable heater assembly so that a selected portion of said wick end is heated to control the evaporation rate as desired according to the application being made.

17. The device of claim 16 including an adjustable connection operatively associated with said movable heater assembly for positioning said heating element at a selected axial position corresponding to said portion of said wick end desired to be heated to adjust the degree of evaporation.

18. The device of claim 17 wherein said movable heater assembly includes a support carrier for said heating element, and including a locking connection for removably affixing said heating element to said carrier.

19. The device of claim 18 wherein said carrier includes a guide arm extending transverse of said housing having an arm end received in a slot opening formed in said housing for access from the outside of the housing, and said adjustable connection includes a plurality of indexed connections for stationarily affixing said carrier relative to said housing.

20. The device of claim 16 wherein said heating element includes a ceramic block having a wick passage formed in said ceramic block so that said ceramic block may selectively surround said wick end as said movable heater assembly is moved.

* * * * *